United States Patent
Mukai (10) Patent No.: US 12,211,186 B2
(45) Date of Patent: Jan. 28, 2025

(54) VIDEO PROCESSING APPARATUS, VIDEO PROCESSING METHOD, AND RECORDING MEDIUM

(71) Applicant: NIKON CORPORATION, Tokyo (JP)

(72) Inventor: Mariko Mukai, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 249 days.

(21) Appl. No.: 17/603,370

(22) PCT Filed: Apr. 17, 2019

(86) PCT No.: PCT/JP2019/016439
§ 371 (c)(1),
(2) Date: Oct. 13, 2021

(87) PCT Pub. No.: WO2020/213085
PCT Pub. Date: Oct. 22, 2020

(65) Prior Publication Data
US 2022/0215514 A1    Jul. 7, 2022

(51) Int. Cl.
*G06T 5/73*    (2024.01)
*G06T 3/40*    (2024.01)
*G06T 15/00*   (2011.01)

(52) U.S. Cl.
CPC .......... *G06T 5/73* (2024.01); *G06T 3/40* (2013.01); *G06T 15/005* (2013.01); *G06T 2207/30041* (2013.01)

(58) Field of Classification Search
CPC . G06T 2207/30041; G06T 3/40; G06T 5/003; G06T 15/005; G06T 2207/10016; G06T 2207/10024; G06T 7/33
See application file for complete search history.

(56) References Cited

U.S. PATENT DOCUMENTS

| | | |
|---|---|---|
| 2008/0212026 A1 | 9/2008 | Molnar et al. |
| 2010/0201800 A1* | 8/2010 | Yamamoto ............... G06T 7/42 348/79 |

(Continued)

FOREIGN PATENT DOCUMENTS

| | | |
|---|---|---|
| JP | 2010-502394 A | 1/2010 |
| JP | 2013-506523 A | 2/2013 |

(Continued)

OTHER PUBLICATIONS

International Search Report with English translation and Written Opinion issued in corresponding application No. PCT/JP2019/016439 dated Jul. 10, 2019.

(Continued)

*Primary Examiner* — Ming Wu
(74) *Attorney, Agent, or Firm* — Foley & Lardner LLP (57) ABSTRACT

A video processing apparatus includes: an acquisition unit configured to acquire subject eye video data; an elimination unit configured to eliminate positional offset resulting from involuntary eye movement from the subject eye video data on the basis of the subject eye video data acquired by the acquisition unit; an emphasis unit configured to perform emphasis on the subject eye video data that was subjected to the elimination performed by the elimination unit; and an output unit configured to output the subject eye video data that was subjected to the emphasis by the emphasis unit.

21 Claims, 10 Drawing Sheets

(56) References Cited

U.S. PATENT DOCUMENTS

| | | |
|---|---|---|
| 2012/0195486 A1 | 8/2012 | Kirenko et al. |
| 2013/0010259 A1* | 1/2013 | Carnevale .............. A61B 3/102 |
| | | 351/209 |
| 2014/0039276 A1 | 2/2014 | Hattangadi et al. |
| 2014/0072229 A1 | 3/2014 | Wadhwa et al. |
| 2014/0354794 A1 | 12/2014 | Imamura |
| 2016/0191882 A1 | 6/2016 | Nakajima |
| 2016/0309997 A1 | 10/2016 | Imamura |
| 2018/0096119 A1 | 4/2018 | Yun et al. |
| 2018/0098683 A1* | 4/2018 | Kikuchi ............... A61B 1/3132 |
| 2019/0050985 A1* | 2/2019 | Den Brinker ........ A61B 5/0261 |
| 2019/0094904 A1* | 3/2019 | Yonemoto ................. G06F 1/04 |
| 2020/0121192 A1 | 4/2020 | Fukunishi et al. |

FOREIGN PATENT DOCUMENTS

| | | |
|---|---|---|
| JP | 2013-198719 A | 10/2013 |
| JP | 2015-527136 A | 9/2015 |
| JP | 2016-120262 A | 7/2016 |
| JP | 2016-202880 A | 12/2016 |
| JP | 2017-46976 A | 3/2017 |
| JP | 2017-118919 A | 7/2017 |
| JP | 2019-42263 A | 3/2019 |
| WO | WO2019/003285 A1 | 1/2019 |

OTHER PUBLICATIONS

JP Decision of Refusal Issued in Corresponding Japanese Patent Application No. 2023-117738 Dated Dec. 10, 2024 (6 pages).

* cited by examiner

VIDEO PROCESSING APPARATUS, VIDEO PROCESSING METHOD, AND RECORDING MEDIUM

BACKGROUND

The present invention relates to a video processing apparatus, a video processing method, and a video processing program.

WO 2019/003285 discloses an image processing device, an image processing method, and a program by which changes due to biological factors can be viewed. In WO 2019/003285, involuntary eye movement is not considered.

SUMMARY

A video processing apparatus of the disclosure technology comprise: an acquisition unit configured to acquire subject eye video data; an elimination unit configured to eliminate positional offset resulting from involuntary eye movement from the subject eye video data on the basis of the subject eye video data acquired by the acquisition unit; an emphasis unit configured to perform emphasis on the subject eye video data that was subjected to the elimination performed by the elimination unit; and an output unit configured to output the subject eye video data that was subjected to the emphasis by the emphasis unit.

In video processing method of the disclosure technology, a processor executes: an acquisition process of acquiring subject eye video data; an elimination process of eliminating positional offset resulting from involuntary eye movement from the subject eye video data on the basis of the subject eye video data acquired by the acquisition process; an emphasis process of performing emphasis on the subject eye video data that was subjected to the elimination performed by the elimination process; and an output process of outputting the subject eye video data that was subjected to the emphasis by the emphasis process.

A video processing program of the disclosure technology causes a processor to execute: an acquisition process of acquiring subject eye video data; an elimination process of eliminating positional offset resulting from involuntary eye movement from the subject eye video data on the basis of the subject eye video data acquired by the acquisition process; an emphasis process of performing emphasis on the subject eye video data that was subjected to the elimination performed by the elimination process; and an output process of outputting the subject eye video data that was subjected to the emphasis by the emphasis process.

DETAILED DESCRIPTION OF THE EMBODIMENTS

Example of Involuntary Eye Movement Elimination and Video Emphasis

Figure 1:
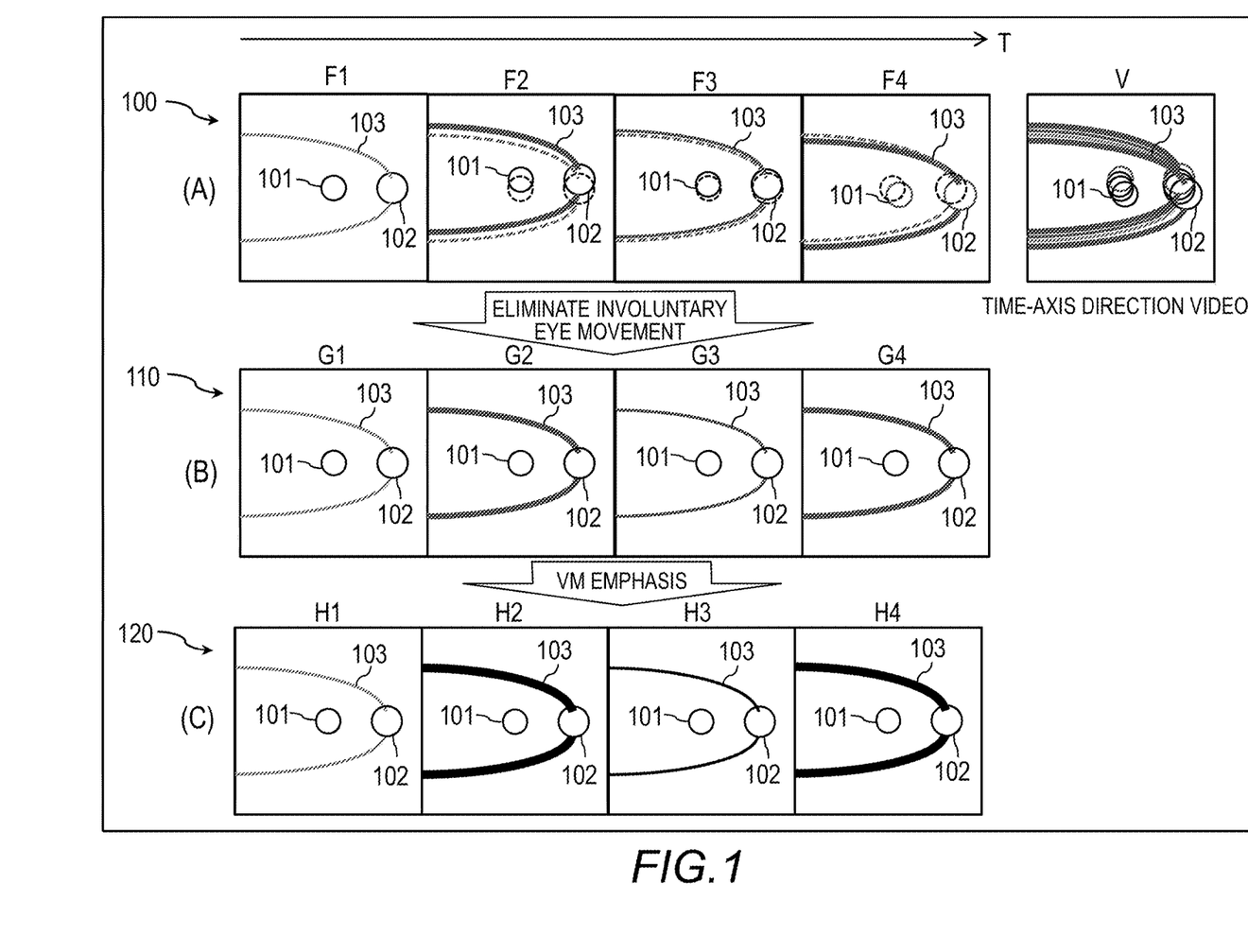
FIG. 1 is a descriptive view showing an example of involuntary eye movement elimination and video magnification (video emphasis).

FIG. 1 is a descriptive view showing an example of involuntary eye movement elimination and video magnification (video emphasis). T is the time axis. The arrow of the time axis T is the time axis direction, or in other words, the direction in which time progresses. (A) shows fundus video data 100. The fundus video data 100 is video data attained by capturing a region including a macula 101, an optic disc 102, and blood vessels 103 of the fundus of a subject. The fundus video data 100 includes fundus image frames F1 to F4 in chronological order, for example. The smaller the suffix number is, the earlier the frame is. If not distinguishing between the fundus image frames F1 to F4, the fundus image frames are referred to as the fundus image frames F. For ease of description, only fundus image frames up to the fundus image frame F4 are included here, but there may be fundus image frames F beyond the fundus image frame F4.

The fundus image frames F1 to F4 include, as image data, the macula 101, the optic disc 102, and the blood vessels 103. Tissue other than the macula 101, the optic disc 102, and the blood vessels 103 are omitted from the depiction. The fundus image frame F1 serves as a reference frame for position-matching the fundus image frames F2 to F4. The fundus image frames F2 to F4 depict the macula 101, the optic disc 102, and the blood vessels 103 of the fundus image frame F1 with dotted lines.

The fundus is imaged in a state where the imaging device is fixed in place, and thus, the macula 101, the optic disc 102, and the blood vessels 103 of the fundus image frames F2 to F4 are offset from the positions of the macula 101, the optic disc 102, and the blood vessels 103 of the fundus image frame F1 due to involuntary eye movement.

Involuntary eye movement is movement of the eye, referred to as a saccade, in which the gaze repeatedly shifts rapidly (approximately 100-500 instances per second) over short periods of time (approximately 20-80 ms). Depending on the dynamic characteristics of the involuntary eye movement, involuntary eye movement can be classified into the following types: microsaccades in which the eye movement is relatively large and fast; drift, in which the movement is large and slow; and tremors, in which the movement is small and high frequency.

Also, the amount of blood flowing through the blood vessels 103 increases or decreases depending on the heartbeat. For example, the amount of blood flowing through the blood vessels 103 is greater in the fundus image frames F2 and F4 compared to the fundus image frames F1 and F3. Thus, the blood vessels 103 are wider and darker in color in the fundus image frames F2 and F4 than in the fundus image frames F1 and F3.

In (A), the blood vessels 103 in the fundus image frame F1 are the lightest in color, and the blood vessels 103 in the fundus image frames F2 and F4 are the darkest in color. Also, the color of the blood vessels 103 in the fundus image frame F3 is darker than the blood vessels 103 of the fundus image frame F1 but lighter than the blood vessels 103 of the fundus image frames F2 and F4.

Video data V is the fundus video data 100 from playing back the fundus image frames F1 to F4 in the time direction. The video data V is the fundus video data 100 at the display timing of the fundus image frame F4, and the macula 101, the optic disc 102, and the blood vessels 103 of the previous fundus image frames F1 to F3 are visible as residual images. Thus, a physician who is the user would have difficulty knowing whether the width and color of the blood vessels 103 is changing due to the heartbeat or involuntary eye movement. That is, in reality, it is difficult to distinguish between changes in the width and color of the blood vessels 103 and positional shifts and color changes in the blood vessels between frames resulting from involuntary eye movement.

(B) shows fundus video data 110 in which involuntary eye movement has been eliminated from the fundus video data 100 of (A). The fundus video data 110 includes fundus image frames G1 to G4 in chronological order. The fundus image frames G1 to G4 are frames in which involuntary eye movement was eliminated from the fundus image frames F1 to F4, respectively, through image processing. If not distinguishing between the fundus image frames G1 to G4, the fundus image frames are referred to as the fundus image frames G.

By correcting for positional offset between frames resulting from involuntary eye movement, the involuntary eye movement is eliminated, and thus, the macula 101, the optic disc 102, and the blood vessels 103 of the fundus image frames G2 to G4 are, respectively, displayed in the same positions as the macula 101, the optic disc 102, and the blood vessels 103 of the fundus image frame F1, which are indicated with the dotted lines in the fundus image frames F2 to F4. On the other hand, movement and color changes in the blood vessels 103 resulting from the heartbeat are not eliminated. Thus, confusion between involuntary eye movement and pulsation and color changes in specific tissue such as the blood vessels 103 is mitigated, and the user such as a physician can observe the pulsation and color changes of the specific tissue without the influence of the involuntary eye movement.

(C) shows fundus video data 120 generated by performing processing in which the blood vessels 103 are subjected to video emphasis as specific tissue within the fundus video data 110 of (B), with changes in the width and color of the blood vessels 103 being displayed with emphasis. The fundus video data 120 includes fundus image frames H1 to H4 in chronological order. The fundus image frames H1 to H4 are frames generated by performing video emphasis on the fundus image frames G1 to G4, respectively, through image processing. If not distinguishing between the fundus image frames H1 to H4, the fundus image frames are referred to as the fundus image frames H. Video emphasis is a technique by which minute changes in movement that are one pixel or less in the footage and small changes in color and movement are displayed with emphasis. By performing video emphasis on the fundus video, it is possible to display with emphasis changes in the width (movement) and color of the blood vessels resulting from the heartbeat. As a result, the user such as a physician can view with ease the color changes in the blood vessel 103 resulting from the heartbeat.

Below, the mechanism by which the involuntary eye movement is eliminated will be described.

<Ophthalmic System>

Figure 2:
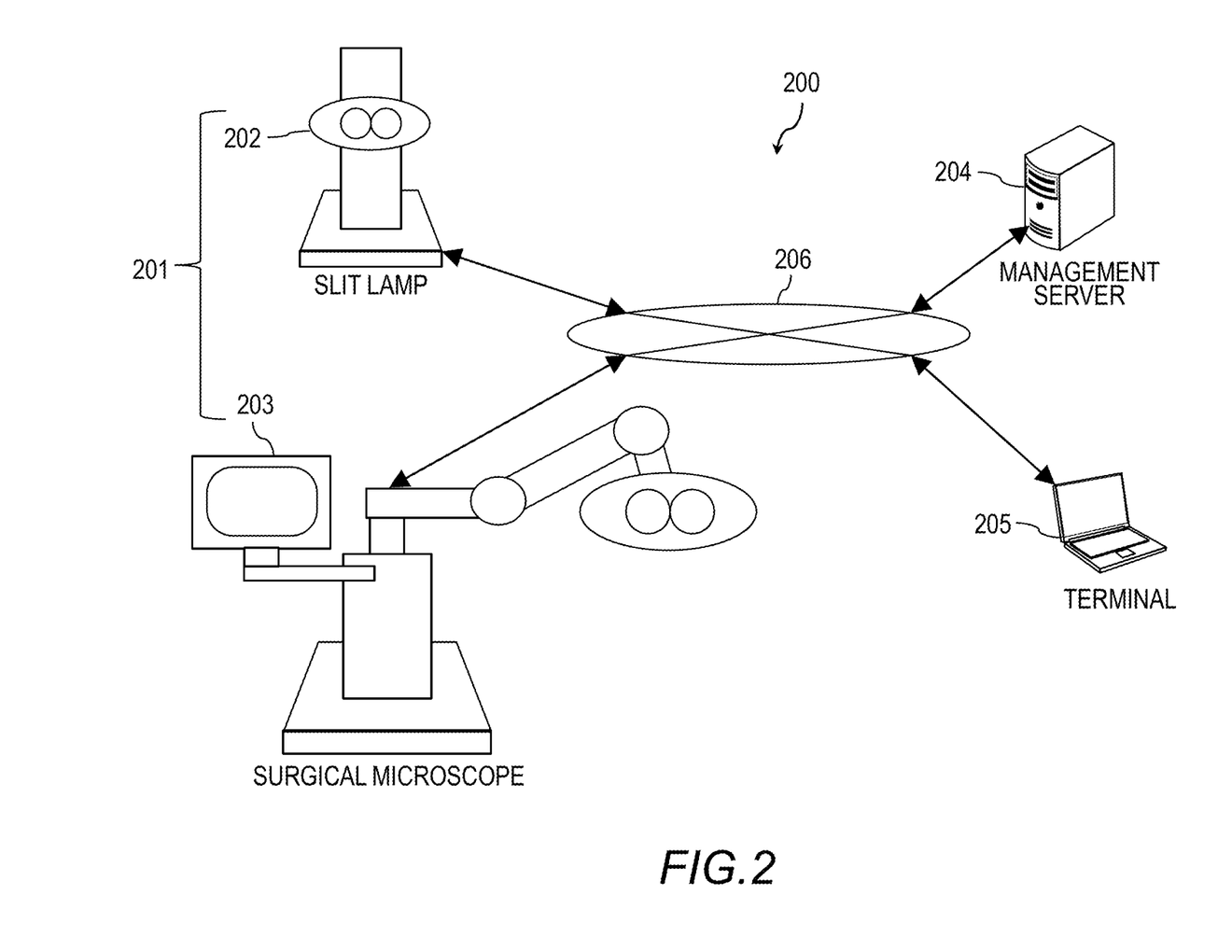
FIG. 2 is a system configuration drawing showing an example of an ophthalmic system.

FIG. 2 is a system configuration drawing showing an example of an ophthalmic system. In the ophthalmic system 200, a slit lamp 202 (slit lamp microscope) and a surgical microscope 203 constituting an ophthalmic apparatus 201, a management server 204, and a terminal 205 are connected in a manner enabling communication therebetween via a network 206 such as a LAN (local area network), a WAN (wide area network), or the internet. The slit lamp 202 is a microscope in which a subject eye is illuminated with slit light, and an illuminated cross section of the subject eye is imaged and observed from the side. The surgical microscope 203 is a microscope specialized for surgery. Both the slit lamp 202 and the surgical microscope 203 can generate, transmit, store, and display the fundus video data 100, 110, and 120 as subject eye video data. As long as the ophthalmic apparatus 201 can image the subject eye of the patient, the ophthalmic apparatus 201 may be a fundus camera, a scanning laser ophthalmoscope (SLO), or an optical coherence tomography (OCT) device.

The management server 204 acquires and stores fundus video data from the ophthalmic apparatus 201, or transmits the fundus video data to the ophthalmic apparatus 201 or the terminal 205. The terminal 205 receives and plays back the fundus video data from the ophthalmic apparatus 201 or the management server 204, or transmits the fundus video data 100, 110, and 120 to the ophthalmic apparatus 201 or the management server 204.

At least one of the ophthalmic apparatus 201, the management server 204, and the terminal 205 can execute the involuntary eye movement elimination described in FIG. 1, and at least one of the ophthalmic apparatus 201, the management server 204, and the terminal 205 can execute the video emphasis described in FIG. 1. That is, the involuntary eye movement elimination and the video emphasis may be executed by the same device or by different devices.

Computer Hardware Configuration Example

Next, a computer hardware configuration example will be described. A computer is a collective term for the ophthalmic apparatus 201, the management server 204, and the terminal 205 shown in FIG. 2. If the computer is the ophthalmic apparatus 201, then a light source, an optical system, and a sensor (not shown) are included.

Hardware Configuration Example of Computer

Figure 3:
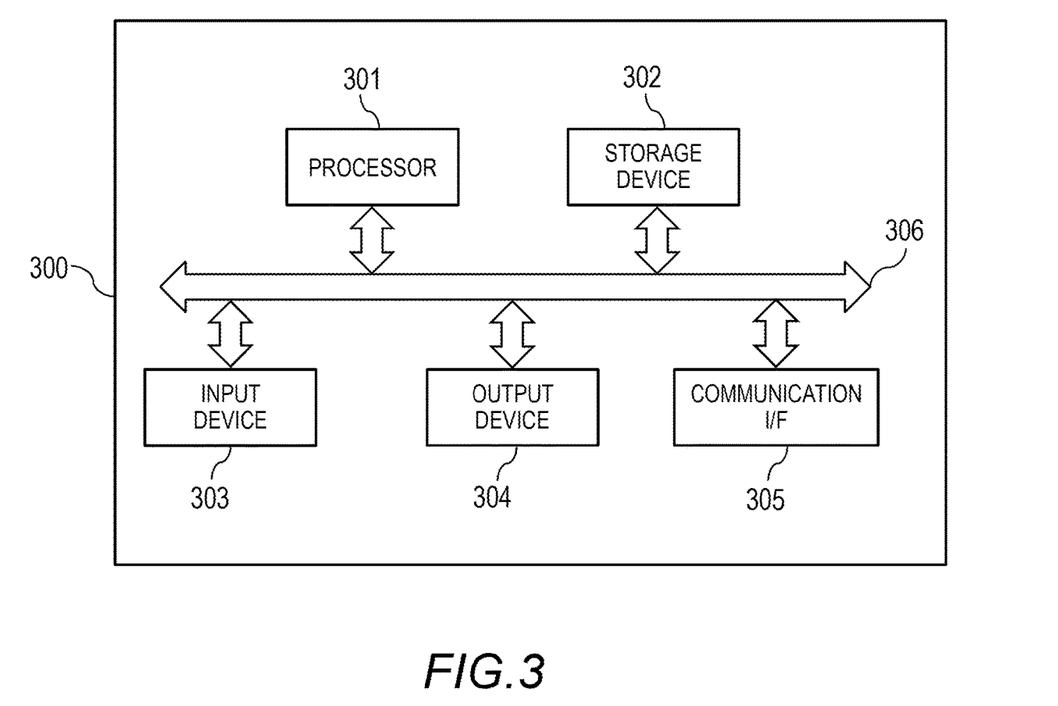
FIG. 3 is a block diagram for illustrating a hardware configuration example of each of a computer.

FIG. 3 is a block diagram for illustrating a hardware configuration example of each of a computer. A computer 300 includes a processor 301, a storage device 302, an input device 303, an output device 304, and a communication interface (communication IF) 305. The processor 301, the storage device 302, the input device 303, the output device 304, and the communication IF 305 are coupled to one another through a bus 306. The processor 301 is configured to control the computer 300. The storage device 302 serves as a work area for the processor 301. The storage device 302 is also a non-transitory or transitory recording medium configured to store various programs and various kinds of data. Examples of the storage device 302 include a read only memory (ROM), a random access memory (RAM), a hard disk drive (HDD), and a flash memory. The input device 303 is configured to input data. Examples of the input device 303 include a keyboard, a mouse, a touch panel, a numeric keypad, and a scanner. The output device 304 is configured to output data. Examples of the output device 304 include a display, and a printer. The communication IF 305 is coupled to the network 206, and is configured to transmit and receive data.

Functional Configuration Example of Video Processing Device

Figure 4:
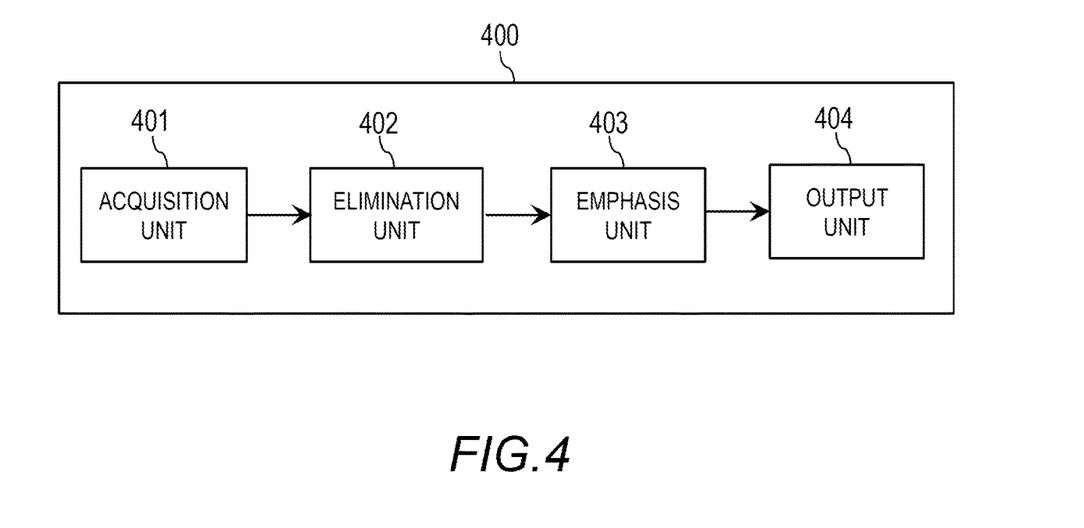
FIG. 4 is a block diagram showing a mechanical configuration example of a video processing apparatus.
Figure 5:
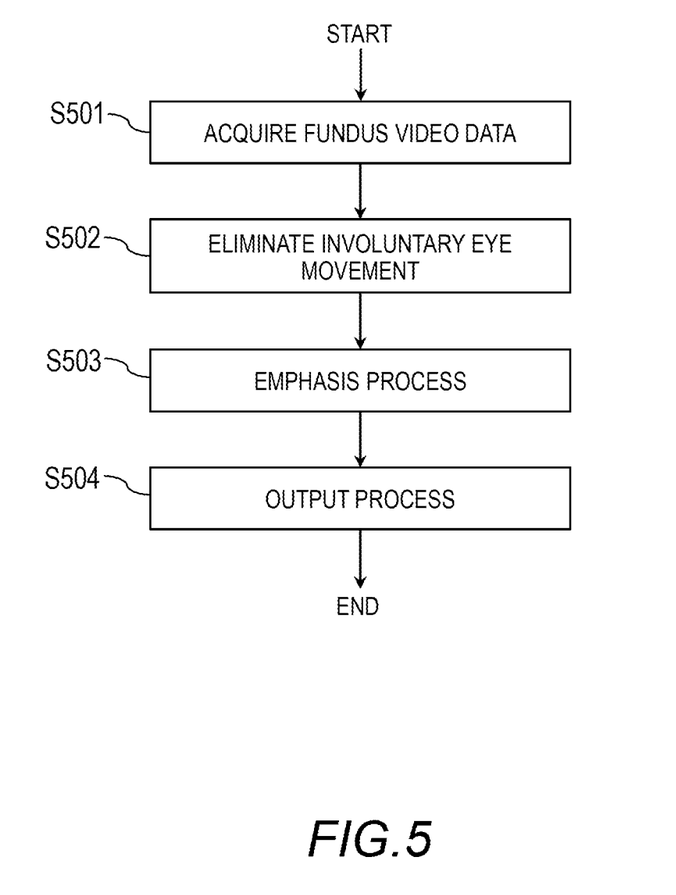
FIG. 5 is a flowchart showing an example of image processing steps performed by the video processing apparatus.

FIG. 4 is a block diagram showing a mechanical configuration example of a video processing apparatus, and FIG. 5 is a flowchart showing an example of image processing steps performed by the video processing apparatus. In FIG. 4, the video processing apparatus 400 has an acquisition unit 401, an elimination unit 402, an emphasis unit 403, and an output unit. The video processing apparatus 400 has at least one of the elimination unit 402 and the emphasis unit 403 in a computer 300. The video processing apparatus 400 is constituted of one computer 300, or a plurality of linked computers 300.

The acquisition unit 401, the elimination unit 402, the emphasis unit 403, and the output unit are specifically realized by a processor 301 executing programs stored in a storage device 302 shown in FIG. 3, for example.

The acquisition unit 401 acquires the fundus video data 100 from the storage device 302 in the video processing apparatus 400 or from another computer 300 outside of the video processing apparatus 400 (step S501). The elimination unit 402 eliminates involuntary eye movement from the fundus video data 100 on the basis of the fundus video data 100 acquired by the acquisition unit 401, or in other words, corrects the positional offset in the fundus region between frames resulting from involuntary eye movement to eliminate the effect of involuntary eye movement from the video data (step S502).

The emphasis unit 403 executes emphasis processing through VM for the fundus video data 110 in which the effect of involuntary eye movement was eliminated by the elimination unit 402 (step S503). Specifically, for example, the emphasis unit 403 emphasizes specific frequency components in the time direction. The emphasis unit 403 may emphasize the entirety of each of the fundus image frames F of the fundus video data 100, or may emphasize regions including specific tissue such as the macula 101, the optic disc 102, the blood vessels 103, or the like.

The output unit 404 outputs the fundus video data 120 in which the specific tissue was emphasized by the emphasis unit 403 (step S504). Specifically, the output unit 404 displays the fundus video data 120 in the display device of the video processing apparatus 400, or transmits the fundus video data 120 from the video processing apparatus 400 to another computer 300, for example.

Figure 6A:
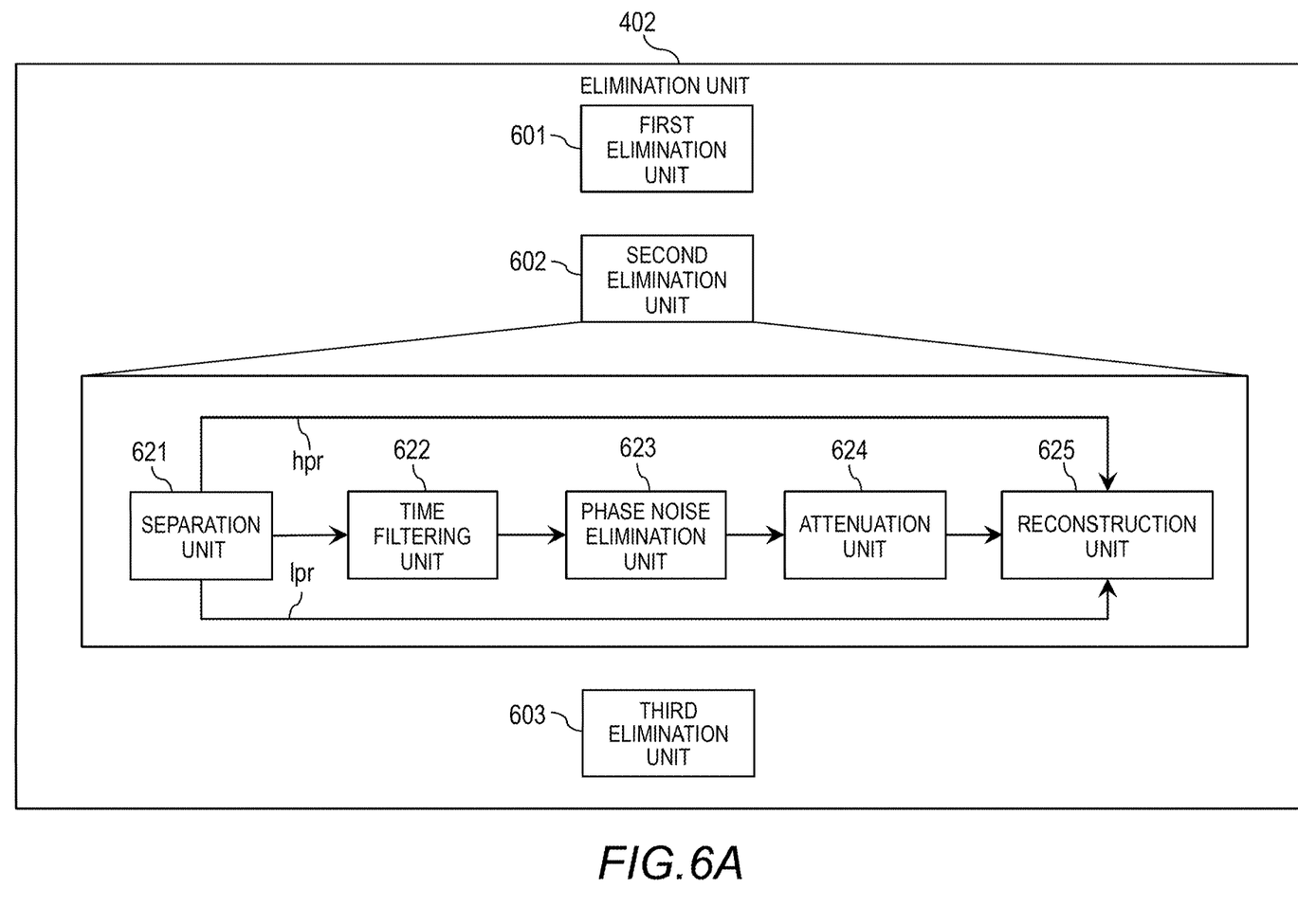
FIG. 6A is a block diagram showing a detailed functional configuration example of the elimination unit.

FIG. 6A is a block diagram showing a detailed functional configuration example of the elimination unit 402. The elimination unit 402 includes a first elimination unit 601, a second elimination unit 602, and a third elimination unit 603. First, the first elimination unit 601 will be described.

The first elimination unit 601 eliminates involuntary eye movement in order for the emphasis unit 403 to emphasize the movement and color change of specific tissue such as the blood vessels 103. Specifically, the first elimination unit 601 is also an involuntary eye movement elimination unit, for example. As described in FIG. 1, the first elimination unit 601 sets the fundus image frame F1 as the reference frame, and executes position-matching with the other fundus image frames F2 to F4 as comparison frames. Here, the reference frame was set as the oldest fundus image frame F1 among the fundus image frames F1, but the reference frame may be set to any of the fundus image frames F2 to F4. Setting the oldest fundus image frame F1 as the reference frame would improve real-time processing.

As a result of the positional offset of the fundus due to involuntary eye movement being corrected through position-matching of the frames, the effect of involuntary eye movement is eliminated from the corrected video data, and the blood vessels 103, the optic disc 102, and the macula 101 are in the same position for all of the frames. Thus, the emphasis unit 403, to be described later, emphasizes the change in width and color of the blood vessels 103 resulting from the heartbeat.

Position-matching between the reference frame and the comparison frames is executed through non-rigid position-matching using an affine transformation matrix including transformation through translation, rotation, and expansion/contraction. Also, the elimination unit 402 may use an algorithm such as scale-invariant feature transform (SIFT) or speeded up robust features (SURF), which is a speeded up version of SIFT.

Additionally, the first elimination unit 601 may use, as the evaluation function, the sum of squared differences (SSD) for pixel values at the same position, the sum of absolute differences (SAD) for pixel values at the same position, mutual information, or cross-correlation in order to perform position-matching between the reference frame and comparison frames. If mutual information or cross-correlation is used, for example, then the greater than 0 the correlation value is, the more similar the reference frame and the comparison frames are, and the less the correlation value is, the less similar the reference frame and the comparison frames are.

Thus, by executing position-matching between the reference frame and the comparison frames, the positions of the macula 101, the optic disc 102, and the blood vessels 103 of the fundus image frames F2 to F4 that are the comparison frames of FIG. 1 are made to match the respective positions of the macula 101, the optic disc 102, and the blood vessels 103 of the reference frame (fundus image frame F1) depicted with the dotted lines. As a result, the positions of the macula 101, the optic disc 102, and the blood vessels 103 match in the fundus image frames F1 to F4, and therefore, involuntary eye movement is eliminated from the fundus video data 100.

Also, the first elimination unit 601 may eliminate, from the fundus video data 100, comparison frames in which the above-mentioned correlation value is less than or equal to a threshold. A comparison frame with a correlation value less than or equal to the threshold has a low degree of similarity to the reference frame, and thus, can be said to be frames showing microsaccades, which are a relatively large and fast eye movements, microsaccades being one of the dynamic characteristics of the involuntary eye movement. Thus, by eliminating comparison frames with a correlation value less than or equal to the threshold from the fundus video data 100, the first elimination unit 601 can generate the fundus video data 110 in which microsaccades are not displayed.

Next, the second elimination unit 602 will be described. The second elimination unit 602 executes elimination processing for the emphasis unit 403 to emphasize only the color change, among the movement and color change, of specific tissue such as the blood vessels 103. Specifically, the second elimination unit 602 has a separation unit 621, a time filtering unit 622, a phase noise elimination unit 623, an attenuation unit 624, and a reconstruction unit 625, for example.

The separation unit 621 uses a known filtering process such as complex steerable pyramids to separate the fundus image frames G into a high frequency component hpr, a low frequency component lpr, and a plurality of orthogonal components every time a fundus image frame G that was subjected to involuntary eye movement elimination by the first elimination unit 601 is inputted.

That is, the separation unit 621 separates localized wave amplitudes (high frequency component hpr, low frequency component lpr) from the phases (plurality of orthogonal components) of the wave. The separation unit 621 outputs the high frequency component hpr and the low frequency component lpr to the reconstruction unit 625 and outputs the plurality of orthogonal components to the time filtering unit 622.

The time filtering unit 622 independently filters, by time, the phases (plurality of orthogonal components) of the fundus image frames F by position, direction, and scale. The phase noise elimination unit 623 applies spatial smoothing that is weighted by amplitude to increase the S/N ratio of the phases.

The attenuation unit 624 attenuates the phases that were band-passed by time by the time filtering unit 622. As a result, movement of specific tissue (e.g., the blood vessels 103) due to errors (corresponding to heartbeats) occurring due to position-matching by the first elimination unit 601 is suppressed. The reconstruction unit 625 reconstructs the fundus image frames G using the output from the attenuation unit 624, the high frequency component hpr, and the low frequency component lpr. Thus, the reconstructed fundus image frames G are image frames in which the movement of specific tissue is suppressed.

Next, the third elimination unit 603 will be described. The third elimination unit 603 executes elimination processing for the emphasis unit 403 to emphasize only the movement, among the movement and color change, of specific tissue such as the blood vessels 103. Specifically, for example, the third elimination unit 603 accumulates the fundus image frames G that were subjected to involuntary eye movement elimination by the first elimination unit 601, and determines whether the difference in color density in specific tissue (e.g., the blood vessels 103) between two consecutive fundus image frames G is greater than or equal to a threshold. If the difference is greater than or equal to the threshold, then the fundus image frame G with the lighter color density for the specific tissue (e.g., the blood vessels 103), among the two consecutive fundus image frames G, is eliminated.

In the case of the fundus image frames G1 to G4 shown in (B) of FIG. 1, for example, if the difference in color density of the blood vessels 103 between the fundus image frames G1 and G2 is greater than or equal to the threshold, the third elimination unit 603 eliminates the fundus image frame G1, which has the lighter color density for the blood vessels 103. If the difference in color density of the blood vessels 103 between the fundus image frames G2 and G3 and between the fundus image frames G3 and G4 is not greater than or equal to the threshold, the fundus image frames G2 and G3 are not eliminated.

Figure 6B:
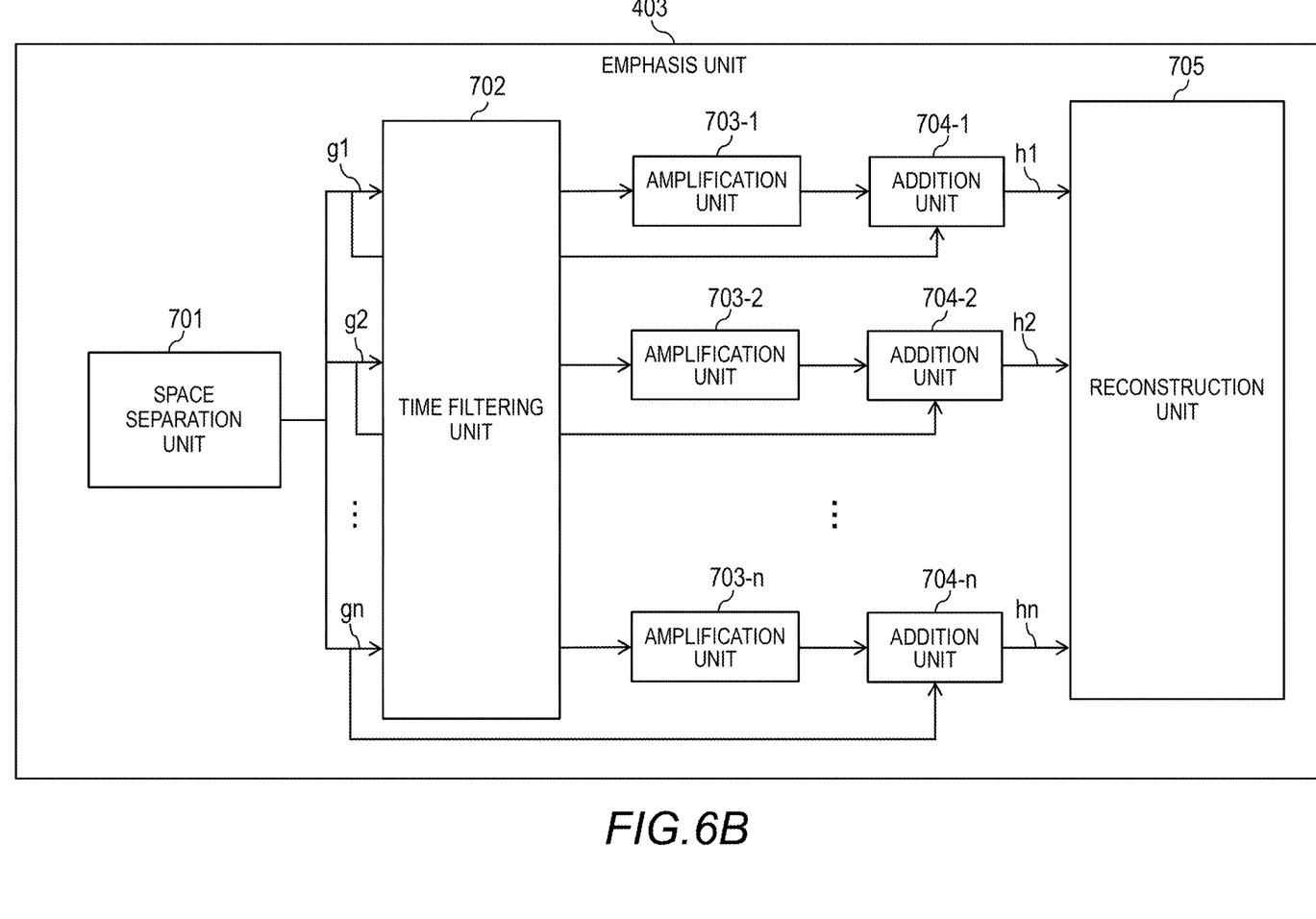
FIG. 6B is a block diagram showing a detailed functional configuration example of the emphasis unit.

FIG. 6B is a block diagram showing a detailed functional configuration example of the emphasis unit 403. The emphasis unit 403 has a spatial separation unit 701, a time filtering unit 702, amplification units 703-1, 703-2 ... 703-n (n being an integer of 2 or greater), addition units 704-1, 704-2 ... 704-n, and a reconstruction unit 705. If not distinguishing between the amplification units 703-1, 703-2 ... 703-n, these are referred to simply as the amplification units 703. If not distinguishing between the addition units 704-1, 704-2 ... 704-n, these are referred to simply as the addition units 704. First, the spatial separation unit 701 will be described.

The spatial separation unit 701 separates the fundus image frames G into a plurality of different spatial frequency bands (band 1, band 2 ... band n) every time a fundus image frame G subjected to involuntary eye movement elimination by the elimination unit 402 is inputted. A known filtering process such as bandpass filters and complex steerable pyramids can be used. The spatial frequency increases in the order of the band 1, the band 2 ... the band n. The image data g1 allocated to the band 1, the image data g2 allocated to the band 2 ... and the image data gn allocated to the band n by the spatial separation unit 701 are outputted to the time filtering unit 702.

Next, the time filtering unit 702 uses a known filtering process such as a second-order infinite impulse response (IIR) filter to extract 60-80 kHz frequency components, which are frequencies at which the human heart beats, from the image data g1, g2 ... gn.

The image data g1 that has passed through the time filtering unit 702 is amplified on the basis of an emphasis coefficient set by the amplification unit 703-1. The emphasis coefficient is set to a factor of 10, for example, and the amplitude of the image data g1 is amplified by 10 times. The image data g1 that has passed through the amplification unit 703-1 is added by the addition unit 704-1 to the image data g1 outputted from the spatial separation unit 701 and outputted to the reconstruction unit 705. Similarly, the image data g2 is also outputted to the reconstruction unit 705 via the amplification unit 703-2 and the addition unit 704-2. The image data gn is also outputted to the reconstruction unit 705 via the amplification unit 703-n and the addition unit 704-n.

The emphasis coefficient of the amplification unit 703 is the same for the entirety of the fundus image frame G subjected to involuntary eye movement elimination by the elimination unit 402, but the emphasis coefficient may be set spatially (for each pixel). Specifically, an emphasis region such as the optic disc 102 or the blood vessels 103 is extracted by image processing employing artificial intelligence or the like or by user instruction, and the emphasis coefficient of the pixels of the extracted emphasis region is set to a differing value than other regions in the fundus image frame G. As a result, video emphasis is performed only on the emphasis regions of the fundus image frame G.

The reconstruction unit 705 uses the image data h1, h2 ... hn outputted from the addition units 704-1, 704-2 ... 704-n to reconstruct the fundus image frames G. In this manner, the reconstructed fundus image frames G are the image frames H1 to H4 in which periodic fluctuations resulting from the heartbeat are emphasized for specific tissue.

The user (ophthalmologist or the like) can select among a plurality of video emphasis modes via an input device 303. At least the following video emphasis modes are made available: normal mode in which both movement and color changes are emphasized; color emphasis mode in which only color change is emphasized; and movement emphasis mode in which only movement is emphasized. If normal mode is selected, the fundus video data 100 is subjected by the first elimination unit 601 of the elimination unit 402 to correction of positional offset among frames resulting from involuntary eye movement, and subjected to video emphasis by the emphasis unit 403.

If color mode is selected, the fundus video data 100 is subjected by the first elimination unit 601 of the elimination unit 402 to correction of positional offset among frames resulting from involuntary eye movement, and then movement of specific tissue is eliminated by the second elimination unit 602. Then, video emphasis is performed by the emphasis unit 403.

If movement emphasis mode is selected, the fundus video data 100 is subjected by the first elimination unit 601 of the elimination unit 402 to correction of positional offset among frames resulting from involuntary eye movement, and then color change is eliminated by the third elimination unit 603. Then, video emphasis is performed by the emphasis unit 403.

<Fundus Video Data 120 Subjected to Video Emphasis>

Figure 7:
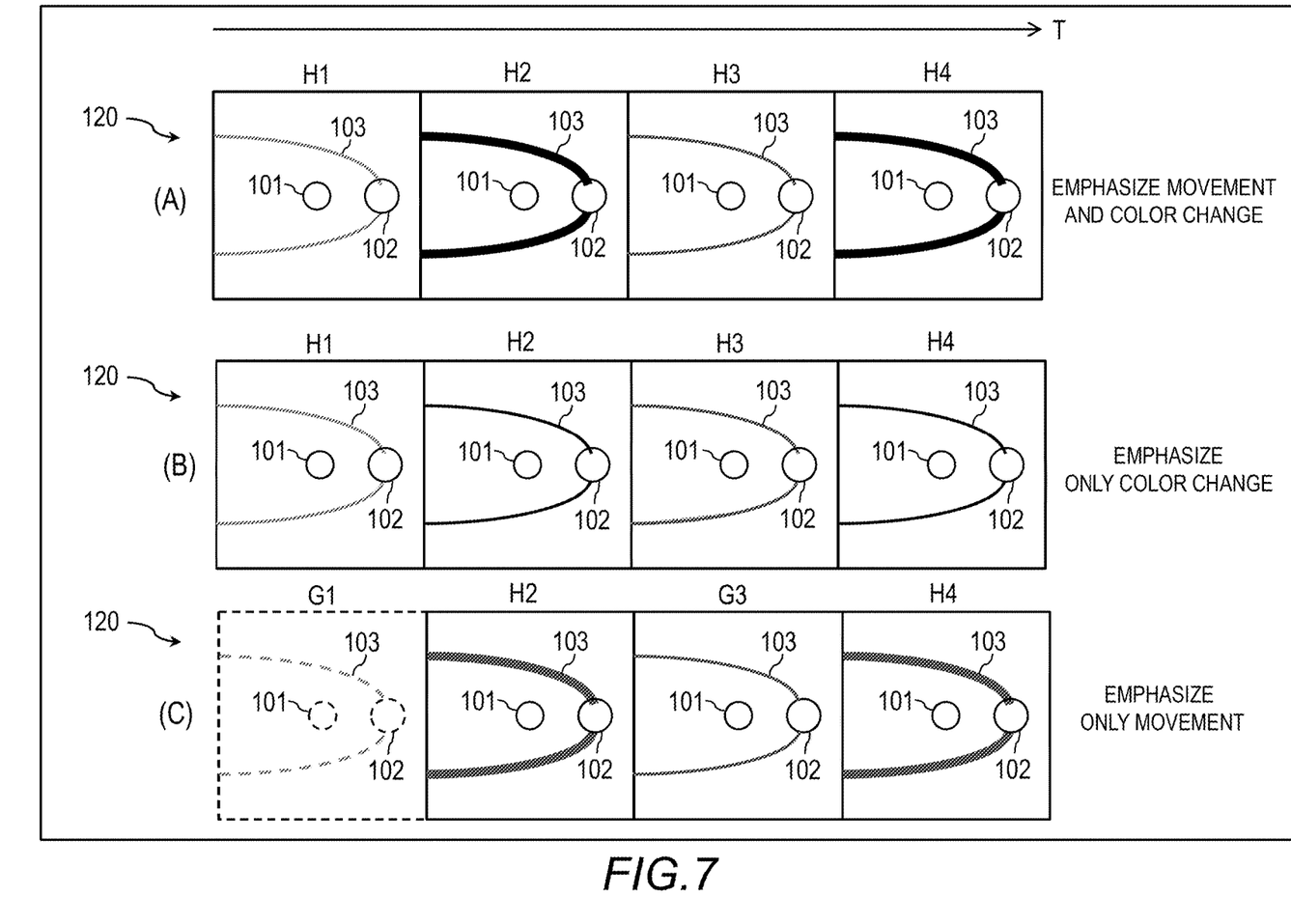
FIG. 7 is a descriptive drawing showing the fundus video data subjected to video emphasis by the emphasis unit.

FIG. 7 is a descriptive drawing showing the fundus video data 120 subjected to video emphasis by the emphasis unit 403. In FIG. 7, periodic fluctuation resulting from the heartbeat is emphasized for specific tissue such as the blood vessels 103. Color change of the blood vessels 103 is observed as a darkening of the blood vessel 103 when blood is sent therethrough and a lightening of the blood vessel 103 thereafter, for example. The movement of the blood vessels 103 involves expansion when blood is pumped therethrough (increased width of the blood vessels 103), and then contraction of the blood vessels 103. Movement and color change tend to be greater for veins than arteries.

(A) shows the fundus video data 120 generated by performing video emphasis on the fundus video data 110 subjected to involuntary eye movement elimination by the first elimination unit 601. In this fundus video data 120, both movement and color changes of the blood vessels 103 are emphasized.

(B) shows the fundus video data 120 generated by performing video emphasis on the fundus video data 110 subjected to involuntary eye movement elimination by the first elimination unit 601 and movement elimination for specific tissue by the second elimination unit 602. In this fundus video data 120, the specific tissue is the blood vessels 103, and only the color change of the blood vessels 103 is emphasized.

(C) shows the fundus video data 120 generated by performing video emphasis on the fundus video data 110 subjected to involuntary eye movement elimination by the first elimination unit 601 and color change elimination by the third elimination unit 603. In this fundus video data 120, the color change is eliminated (the fundus image frame G1 with the lighter color density is eliminated), and only the movement of the blood vessels 103 (change in width of the blood vessels) is emphasized.

Display Examples of Fundus Video Data

Next, display examples of the fundus video data 100, 110, and 120 will be described with reference to FIGS. 8 to 10. The computer 300 may display the fundus video data 110 and 120 in real time during examination, treatment, and surgery, or may read the fundus video data 110 and 120 stored in the storage device 302 and play back the fundus video data, for example. The fundus video data 100 not subjected to involuntary eye movement elimination may be 2-dimensional video data or 3-dimensional video data.

Figure 8:
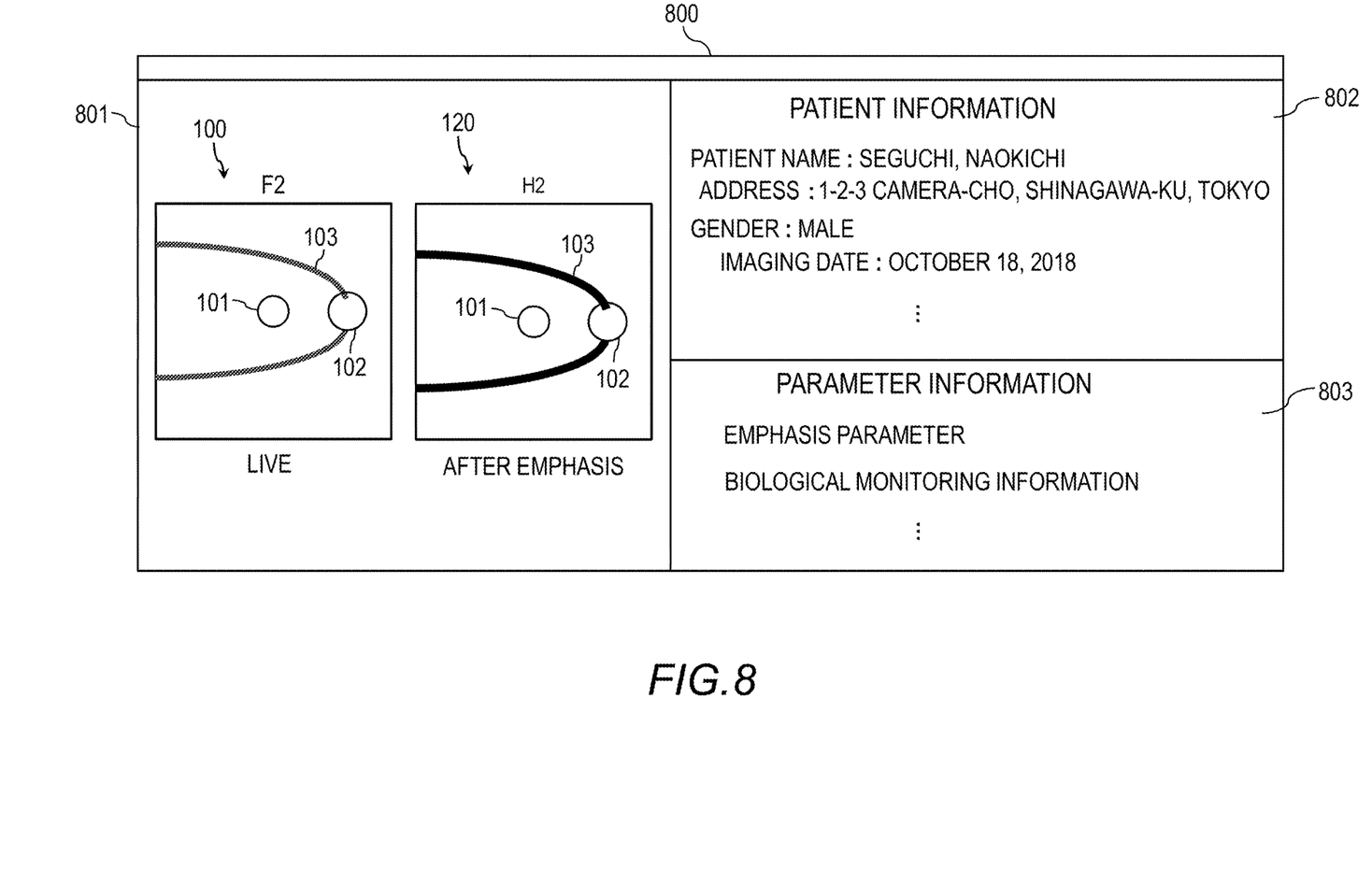
FIG. 8 is a descriptive drawing showing a display example 1 of the fundus video data.

FIG. 8 is a descriptive drawing showing a display example 1 of the fundus video data. A display screen 800 includes a video data display region 801, a patient information display region 802, and a parameter information display region 803. The video data display region 801 displays the fundus video data 100 and 120. Thus, the user can view while comparing the fundus video data 100, which is live footage, and the fundus video data 120, which was subjected to involuntary eye movement elimination and video emphasis.

The patient information display region 802 displays patient information. The patient information is information identifying the patient such as the personal name, the address, and the like. The patient is a person having the subject eye being imaged as the fundus video data 100.

The parameter information display region 803 displays parameter information. The parameter information includes an emphasis parameter and biological monitoring information, for example. The emphasis parameter is a parameter indicating the frequency domain to be emphasized by video emphasis by the emphasis unit 403 and the degree of emphasis. The biological monitoring information is information from monitoring the body of the patient such as the pulse of the patient.

Figure 9:
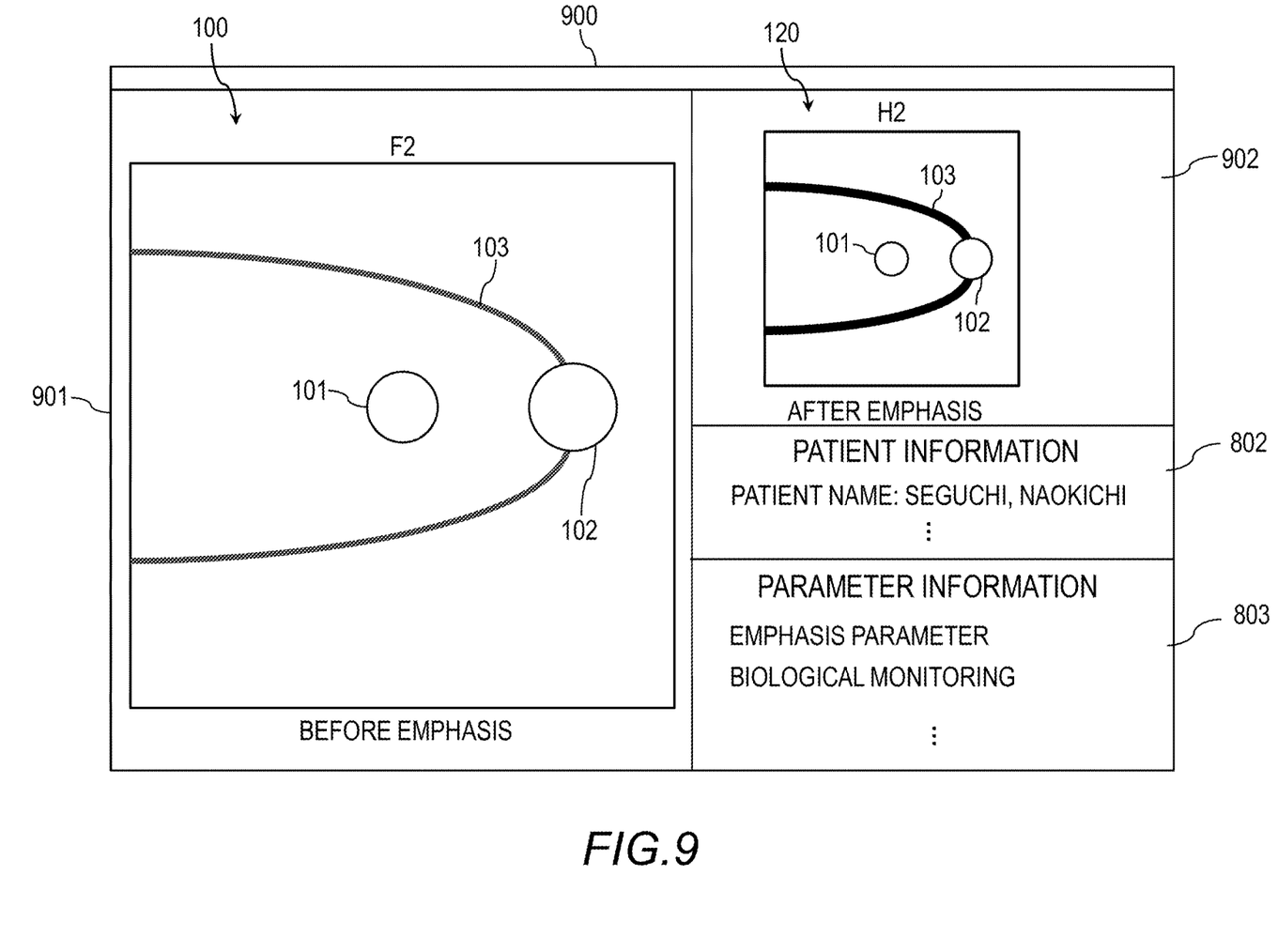
FIG. 9 is a descriptive drawing showing a display example 2 of the fundus video data.

FIG. 9 is a descriptive drawing showing a display example 2 of the fundus video data. A display screen 900 includes a first video data display region 901, a second video data display region 902, the patient information display region 802, and the parameter information display region 803.

The first video data display region 901 displays the fundus video data 100 prior to involuntary eye movement elimination. The first video data display region 901 is the main screen and is larger than the second video data display region 902. The second video data display region 902 displays the fundus video data 120 after involuntary eye movement elimination and video emphasis. The second video data display region 902 is a subscreen and is smaller than the first video data display region 901. As a result, the user can focus on the first video data display region 901 while viewing the second video data display region 902 as necessary.

Figure 10:
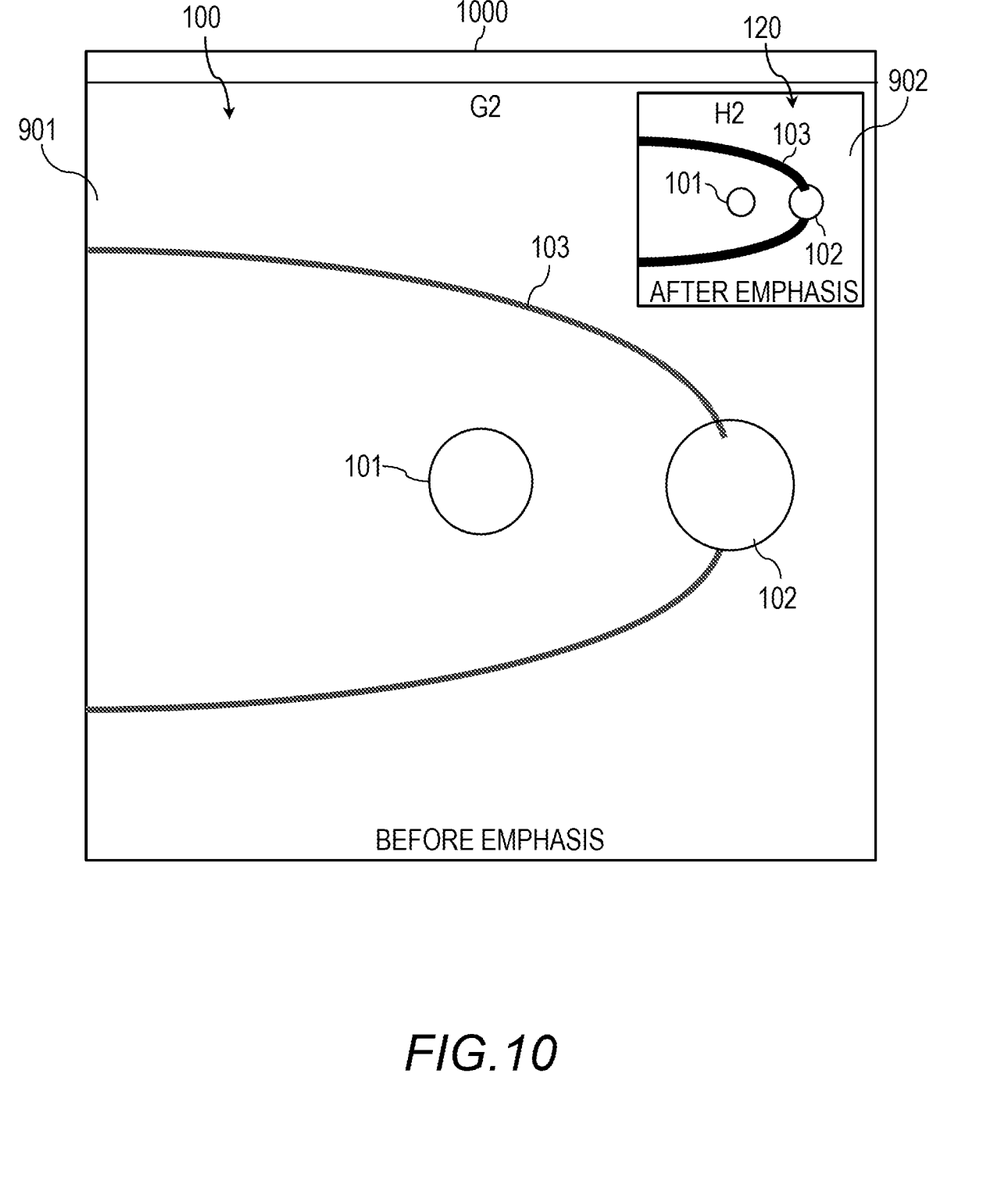
FIG. 10 is a descriptive drawing showing a display example 3 of the fundus video data.

FIG. 10 is a descriptive drawing showing a display example 3 of the fundus video data. The display screen 1000 has the first video data display region 901 that displays the fundus video data 100 prior to involuntary eye movement elimination and the second video data display region 902 that displays the fundus video data 120 after involuntary eye movement elimination and video emphasis, for example. The second video data display region 902 is displayed so as to be superimposed on the upper right corner of the first video data display region 901. As a result, the user can focus on the first video data display region 901 while viewing the second video data display region 902 as necessary.

If a changeover switch such as a foot switch is provided to the ophthalmic apparatus 201, then the display content of the video data display region 801 and the second video data display region 902 may be switched from the fundus video data 120 to the fundus video data 110 or from the fundus video data 110 to the fundus video data 120 according to the changeover switch being switched ON or OFF. As a result, it is possible to see the difference before and after the video emphasis.

Also, in FIGS. 9 and 10, switching may be performed according to the switching of the changeover switch ON or OFF such that the fundus video data 120 is displayed in the first video data display region 901 and the fundus video data 100 is displayed in the second video data display region 902. As a result, it is possible for the user to view the fundus video data 120 in the larger main screen.

Also, if viewing the fundus video data through an eyepiece of the ophthalmic apparatus 201, the fundus video data 110 and 120 may respectively be viewable through either one of the lenses of the eyepiece for each eye. For example, in the case of FIG. 10, the fundus video data 100 is viewed with the right eye and the fundus video data 100 and 120 is viewed with the left eye.

Also, the display screens 800, 900, and 1000 of FIGS. 8 to 10 may display a mode switching button for switching between video emphasis modes, enabling the user to select between the normal mode in which both movement and color changes are emphasized, color emphasis mode in which only color change is emphasized, and movement emphasis mode in which only movement is emphasized. The fundus video data 120 in the selected video emphasis mode is displayed in the video data display region 801 or the second video data display region 902.

Also, the display screens 800, 900, and 1000 of FIGS. 8 to 10 display live video (fundus video data 100 prior to involuntary eye movement elimination), but may display the fundus video data 120 after involuntary eye movement elimination.

In this manner, it is possible to improve flexibility for the user in viewing the video data before and after video emphasis after being subjected to involuntary eye movement elimination.

The present invention is not limited to the content above, and the content above may be freely combined. Also, other aspects considered to be within the scope of the technical concept of the present invention are included in the scope of the present invention.

EXPLANATION OF REFERENCES

100,110,120 fundus video data, 101 macula, 102 optic disc, 103 blood vessel, 200 ophthalmic system, 201 ophthalmic apparatus, 204 management server, 205 terminal, 400 video processing apparatus, 401 acquisition unit, 402 elimination unit, 403 emphasis unit, 404 output unit, 601 first elimination unit, 602 second elimination unit, 603 third elimination unit, 621 separation unit, 622 time filtering unit, 623 phase noise elimination unit, 624 attenuation unit, 625 reconstruction unit, F,G,H fundus image frame

What is claimed is:

1. A video processing apparatus, comprising:
at least one processor configured to operate as:
   an acquisition unit configured to acquire subject eye video data;
   an elimination unit configured to perform position-matching between a plurality of subject eye frames that constitutes the subject eye video data acquired by the acquisition unit, eliminate positional offset resulting from involuntary eye movement between the plurality of subject eye frames, and, after eliminating the positional offset, additionally eliminate the movement of specific tissue within a subject eye caused by eliminating the positional offset;
   an emphasis unit configured to perform emphasis on the subject eye video data that was subjected to the elimination performed by the elimination unit; and
   an output unit configured to output the subject eye video data that was subjected to the emphasis by the emphasis unit,
wherein the positional offset resulting from involuntary eye movement is different than movement of specific tissue within the subject eye,
wherein the emphasis unit is configured to extract frequency components arranged in a time direction from the subject eye video data and emphasize a color change in the specific tissue within the subject eye resulting from the frequency components.

2. The video processing apparatus according to claim 1, wherein the elimination unit is configured to perform position-matching between a first subject eye frame and a second subject eye frame differing from the first subject eye frame, among a subject eye frame group arranged in a time direction that constitutes the subject eye video data, thereby eliminating the positional offset from the subject eye video data.

3. The video processing apparatus according to claim 2, wherein the elimination unit is configured to perform position-matching on the basis of a cross-correlation between the first subject eye frame and the second subject eye frame, thereby eliminating the positional offset from the subject eye video data.

4. The video processing apparatus according to claim 2, wherein the elimination unit is configured to perform position-matching on the basis of a feature value of the first subject eye frame and the second subject eye frame, thereby eliminating the positional offset from the subject eye video data.

5. The video processing apparatus according to claim 1, wherein the output unit is configured to output, to the display device, the subject eye video data that was subjected to emphasis by the emphasis unit.

6. The video processing apparatus according to claim 5, wherein the output unit is configured to output, to the display device, the subject eye video data that was subjected to emphasis and the subject eye video data prior to being subjected to emphasis by the emphasis unit.

7. The video processing apparatus according to claim 6, wherein the subject eye video data prior to being subjected to emphasis is the subject eye video data that was subjected to elimination by the elimination unit.

8. The video processing apparatus according to claim 1, wherein the emphasis unit is configured to emphasize the color change and a width change of blood vessels resulting from the heartbeat.

9. A video processing method,
wherein at least one processor executes;
an acquisition process of acquiring subject eye video data;
an elimination process of performing position-matching between a plurality of subject eye frames that constitutes the subject eye video data acquired by the acquisition process, eliminating positional offset resulting from involuntary eye movement between the plurality of subject eye frames, and, after eliminating the positional offset, additionally eliminating movement of specific tissue within a subject eye caused by eliminating the positional offset;
an emphasis process of performing emphasis on the subject eye video data that was subjected to the elimination performed by the elimination process; and
an output process of outputting the subject eye video data that was subjected to the emphasis by the emphasis process,
wherein the positional offset resulting from involuntary eye movement is different than movement of specific tissue within the subject eye,
wherein the emphasis unit is configured to extract frequency components arranged in a time direction from the subject eye video data and emphasize a color change in the specific tissue within the subject eye resulting from the frequency components.

10. A non-transitory processor-readable recording medium having a video processing program recorded thereon which when executed by a processor causes the processor to execute a method,
the video processing program causing the processor to execute;
an acquisition process of acquiring subject eye video data;
an elimination process of performing position-matching between a plurality of subject eye frames that constitutes the subject eye video data acquired by the acquisition process, eliminating positional offset resulting from involuntary eye movement between the plurality of subject eye frames, and, after eliminating the positional offset, additionally eliminating movement of specific tissue within a subject eye caused by eliminating the positional offset;
an emphasis process of performing emphasis on the subject eye video data that was subjected to the elimination performed by the elimination process; and
an output process of outputting the subject eye video data that was subjected to the emphasis by the emphasis process,
wherein the positional offset resulting from involuntary eye movement is different than movement of specific tissue within the subject eye, and
wherein the emphasis unit is configured to extract frequency components arranged in a time direction from the subject eye video data and emphasize a color change in the specific tissue within the subject eye resulting from the frequency components.

11. A video processing apparatus, comprising:
at least one computer, comprising:
an acquisition unit configured to acquire subject eye video data;
an emphasis elimination unit configured to perform position-matching between a plurality of subject eye frames that constitutes the subject eye video data acquired by the acquisition unit, eliminate positional offset resulting from involuntary eye movement from the subject eye video data, and, after eliminating the positional offset, additionally eliminate a color change in specific tissue within the subject eye, thereby eliminating specific subject eye frame that has a larger color change in specific tissue within the subject eye among the plurality of subject eye frames;
an emphasis unit configured to perform emphasis on the subject eye video data that was subjected to the amendment by the elimination unit; and
an output unit configured to output the subject eye video data that was subjected to the emphasis by the emphasis unit,
wherein the emphasis unit is configured to extract frequency components arranged in a time direction from the subject eye video data and eliminate the color change in the specific tissue within the subject eye resulting from the frequency components.

12. The video processing apparatus according to claim 11, wherein the elimination unit is configured to perform position-matching between a first subject eye frame and a second subject eye frame differing from the first subject eye frame, among a subject eye frame group arranged in a time direction that constitutes the subject eye video data, thereby eliminating the positional offset from the subject eye video data.

13. The video processing apparatus according to claim 11, wherein the elimination unit is configured to perform position-matching on the basis of a cross-correlation between the first subject eye frame and the second subject eye frame, thereby eliminating the positional offset from the subject eye video data.

14. The video processing apparatus according to claim 11, wherein the elimination unit is configured to perform position-matching on the basis of a feature value of the first subject eye frame and the second subject eye frame, thereby eliminating the positional offset from the subject eye video data.

15. The video processing apparatus according to claim 11, wherein the emphasis unit is configured to extract frequency components arranged in a time direction from the subject eye video data and emphasize movement in the specific tissue within the subject eye resulting from the frequency components.

16. The video processing apparatus according to claim 11, wherein the output unit is configured to output, to the display device, the subject eye video data that was subjected to emphasis.

17. The video processing apparatus according to claim 11, wherein the emphasis unit is configured to emphasis changes in the width and color of the blood vessels resulting from the heartbeat.

18. The video processing apparatus according to claim 15, wherein the output unit is configured to output, to the display device, the subject eye video data that was subjected to emphasis and the subject eye video data prior to being subjected to emphasis by the emphasis unit.

19. The video processing apparatus according to claim 18, wherein the subject eye video data prior to being subjected to emphasis is the subject eye video data that was subjected to elimination by the elimination unit.

20. A video processing method,
wherein at least processor executes;
an acquisition process of acquiring subject eye video data;
an elimination process of performing position-matching between a plurality of subject eye frames that constitutes the subject eye video data acquired by an acquisition unit, eliminating positional offset resulting from involuntary eye movement from the subject eye video data, and, after eliminating the positional offset, additionally eliminating a color change in specific tissue within the subject eye, thereby eliminating specific subject eye frame that has a larger color change in specific tissue within the subject eye among the plurality of subject eye frames;
an emphasis process of performing emphasis on the subject eye video data that was subjected to the performance by an elimination unit; and
an output process of outputting the subject eye video data that was subjected to the emphasis by the emphasis process,
wherein the emphasis unit is configured to extract frequency components arranged in a time direction from the subject eye video data and eliminate the color change in the specific tissue within the subject eye resulting from the frequency components.

21. A non-transitory processor-readable recording medium having a video processing program recorded thereon which when executed by a processor causes the processor to execute a method, the video processing program causing the processor to execute;

an acquisition process of acquiring subject eye video data;

an elimination process of performing position-matching between a plurality of subject eye frames that constitutes the subject eye video data acquired by an acquisition unit, eliminating positional offset resulting from involuntary eye movement from the subject eye video data, and, after eliminating the positional offset, additionally eliminating a color change in specific tissue within the subject eye, thereby eliminating specific subject eye frame that has a larger color change in specific tissue within the subject eye among the plurality of subject eye frames;

an emphasis process of performing emphasis on the subject eye video data that was subjected to the performance by an elimination unit; and an output process of outputting the subject eye video data that was subjected to the emphasis by the emphasis process, wherein the emphasis unit is configured to extract frequency components arranged in a time direction from the subject eye video data and eliminate the color change in the specific tissue within the subject eye resulting from the frequency components.

* * * * *